(12) United States Patent
Scott (10) Patent No.: US 7,195,482 B2
(45) Date of Patent: Mar. 27, 2007

(54) DENTAL CURING DEVICE HAVING A HEAT SINK FOR DISSIPATING HEAT

(75) Inventor: Robert R. Scott, Riverton, UT (US)

(73) Assignee: Ultradent Products, Inc., South Jordan, UT (US)

( * ) Notice: Subject to any disclaimer, the term of this patent is extended or adjusted under 35 U.S.C. 154(b) by 141 days.

(21) Appl. No.: 10/749,059

(22) Filed: Dec. 30, 2003

(65) Prior Publication Data

US 2005/0142514 A1    Jun. 30, 2005

(51) Int. Cl.
*A61C 3/00*    (2006.01)
(52) U.S. Cl. ....................................... 433/29
(58) Field of Classification Search .................. 433/29; 250/504 H; 362/119
See application file for complete search history.

(56) References Cited

U.S. PATENT DOCUMENTS

| | | |
|---|---|---|
| 3,310,358 A | 3/1967 | Marcatili |
| 3,666,180 A | 5/1972 | Coobs et al. ............ 240/41.15 |
| 3,704,928 A | 12/1972 | Coombs et al. |
| 3,930,149 A | 12/1975 | French |
| 4,184,196 A | 1/1980 | Moret |
| 4,221,994 A | 9/1980 | Friedman et al. |
| 4,229,658 A | 10/1980 | Gonser |
| 4,245,890 A | 1/1981 | Hartman et al. |
| 4,266,535 A | 5/1981 | Moret |
| 4,281,366 A | 7/1981 | Wurster et al. |
| 4,309,617 A | 1/1982 | Long |
| 4,348,180 A | 9/1982 | Schuss |
| 4,385,344 A | 5/1983 | Gonser ......................... 362/32 |
| 4,392,827 A | 7/1983 | Martin ......................... 433/32 |
| 4,522,594 A | 6/1985 | Stark et al. |
| 4,611,992 A | 9/1986 | Lokken |
| 4,666,405 A | 5/1987 | Ericson |
| 4,666,406 A | 5/1987 | Kanca, III |
| 4,682,950 A | 7/1987 | Dragan |

(Continued)

FOREIGN PATENT DOCUMENTS

WO    WO 00113608    3/2000

OTHER PUBLICATIONS

U.S. Appl. No. 10/973,537, filed Oct. 26, 2004, Robert R. Scott.

(Continued)

*Primary Examiner*—John J Wilson
(74) *Attorney, Agent, or Firm*—Workman Nydegger (57) ABSTRACT

A dental curing device includes an elongate wand housing having proximal and distal ends, a light source disposed at the distal end, electronic circuitry at least partially disposed within the wand housing between the proximal and distal ends, and a heat sink. The light source may comprise one or more LEDs. The heat sink comprises a metallic heat sink portion adjacent to the light source and extending partially through the wand housing, and a polymer-based heat sink portion comprising a thermally conductive polymer-based material adjacent to the metallic heat sink portion. The polymer-based heat sink portion may comprise an epoxy-based resin that at least partially surrounds the electronic circuitry. The polymer-based heat sink portion advantageously extends through a portion of the wand housing designed to be gripped by the user when the dental curing light is in use.

14 Claims, 4 Drawing Sheets

U.S. PATENT DOCUMENTS

| | | | |
|---|---|---|---|
| 4,698,730 A | 10/1987 | Sakai et al. | |
| 4,733,937 A | 3/1988 | Lia et al. | |
| 4,836,782 A | 6/1989 | Gonser | |
| 4,935,665 A | 6/1990 | Murata | |
| 4,948,215 A | 8/1990 | Friedman | |
| 4,963,798 A | 10/1990 | McDermott | |
| 4,992,045 A | 2/1991 | Beisel | 433/32 |
| 5,013,144 A | 5/1991 | Silverglate et al. | |
| 5,013,240 A | 5/1991 | Bailey et al. | |
| 5,017,140 A | 5/1991 | Ascher | |
| 5,043,634 A | 8/1991 | Rothwell, Jr. et al. | |
| 5,046,810 A | 9/1991 | Steiner et al. | 385/38 |
| 5,071,222 A | 12/1991 | Laakmann et al. | |
| 5,115,761 A | 5/1992 | Hood | |
| 5,123,845 A | 6/1992 | Vassiliadis et al. | |
| 5,139,495 A | 8/1992 | Daikuzono | |
| 5,161,879 A | 11/1992 | McDermott | |
| 5,213,103 A * | 5/1993 | Martin et al. | 600/443 |
| 5,275,564 A | 1/1994 | Vassiliadis et al. | |
| 5,285,318 A | 2/1994 | Gleckman | |
| 5,288,231 A | 2/1994 | Kuehn et al. | |
| 5,290,169 A | 3/1994 | Friedman et al. | |
| 5,312,249 A | 5/1994 | Kennedy | |
| 5,328,368 A | 7/1994 | Lansing et al. | |
| 5,348,552 A | 9/1994 | Nakajima et al. | |
| 5,371,826 A | 12/1994 | Friedman | |
| 5,382,799 A | 1/1995 | May | |
| 5,388,988 A | 2/1995 | Goisser et al. | |
| 5,397,892 A | 3/1995 | Abdelqader | |
| 5,415,543 A | 5/1995 | Rozmajzl, Jr. | |
| 5,420,768 A | 5/1995 | Kennedy | 362/119 |
| D361,382 S | 8/1995 | Brunsell et al. | |
| 5,448,323 A | 9/1995 | Clark et al. | |
| 5,457,611 A | 10/1995 | Verderber | 362/32 |
| 5,485,317 A | 1/1996 | Perissinotto et al. | |
| 5,521,392 A | 5/1996 | Kennedy et al. | |
| 5,527,261 A | 6/1996 | Monroe et al. | |
| 5,616,141 A | 4/1997 | Cipolla | |
| 5,634,711 A | 6/1997 | Kennedy | 362/119 |
| 5,660,461 A | 8/1997 | Ignatius et al. | |
| 5,669,769 A | 9/1997 | Disel | |
| D385,051 S | 10/1997 | Wu | |
| D385,630 S | 10/1997 | Lieb et al. | |
| 5,698,866 A | 12/1997 | Doiron et al. | |
| 5,711,665 A | 1/1998 | Adam et al. | |
| 5,733,029 A | 3/1998 | Monroe | |
| 5,749,724 A | 5/1998 | Cheng | |
| 5,759,032 A | 6/1998 | Bartel | |
| 5,762,605 A | 6/1998 | Cane et al. | |
| 5,768,458 A | 6/1998 | Ro et al. | |
| 5,772,643 A | 6/1998 | Howell et al. | |
| 5,782,553 A | 7/1998 | McDermott | |
| 5,791,898 A | 8/1998 | Maissami | |
| 5,797,740 A | 8/1998 | Lundvik | |
| 5,803,729 A | 9/1998 | Tsimerman | |
| 5,880,839 A | 3/1999 | Ishizuka et al. | |
| 5,885,082 A | 3/1999 | Levy | |
| 5,897,314 A | 4/1999 | Hack et al. | 433/29 |
| 5,905,268 A | 5/1999 | Garcia et al. | |
| 5,908,294 A | 6/1999 | Schick et al. | |
| 5,908,295 A | 6/1999 | Kawata | |
| 5,912,470 A | 6/1999 | Eibofner et al. | |
| 5,921,777 A | 7/1999 | Dorman | |
| 5,971,755 A | 10/1999 | Liebermann et al. | |
| 5,975,895 A | 11/1999 | Sullivan | |
| 6,001,058 A | 12/1999 | Sano et al. | |
| 6,008,264 A | 12/1999 | Ostler et al. | |
| 6,019,482 A | 2/2000 | Everett | |
| 6,019,599 A | 2/2000 | Völcker et al. | |
| 6,028,694 A | 2/2000 | Schmidt | |
| 6,033,087 A | 3/2000 | Shozo et al. | |
| 6,033,223 A | 3/2000 | Narusawa et al. | |
| 6,036,336 A | 3/2000 | Wu | |
| 6,059,421 A | 5/2000 | White et al. | |
| 6,068,474 A | 5/2000 | Senn et al. | |
| 6,077,073 A | 6/2000 | Jacob | |
| 6,086,366 A | 7/2000 | Mueller et al. | |
| 6,089,740 A | 7/2000 | Forehand et al. | |
| 6,095,661 A | 8/2000 | Lebens et al. | |
| 6,095,812 A | 8/2000 | Senn et al. | |
| 6,099,520 A | 8/2000 | Shimoji | |
| 6,102,696 A | 8/2000 | Osterwalder et al. | |
| 6,103,203 A | 8/2000 | Fischer | |
| 6,123,545 A | 9/2000 | Eggler et al. | |
| 6,155,823 A | 12/2000 | Nagel | |
| 6,159,005 A | 12/2000 | Herold et al. | |
| 6,200,134 B1 | 3/2001 | Kovac et al. | |
| 6,208,788 B1 | 3/2001 | Nosov | |
| 6,270,343 B1 | 8/2001 | Martin | 433/32 |
| 6,280,187 B1 | 8/2001 | Stone | |
| 6,282,013 B1 | 8/2001 | Ostler et al. | |
| 6,318,996 B1 | 11/2001 | Melikechi et al. | |
| 6,322,358 B1 | 11/2001 | Senn et al. | |
| 6,325,623 B1 | 12/2001 | Melnyk et al. | |
| 6,328,456 B1 | 12/2001 | Mize | |
| 6,331,111 B1 | 12/2001 | Cao | 433/29 |
| 6,361,192 B1 | 3/2002 | Fussell et al. | |
| 6,361,489 B1 | 3/2002 | Tsai | |
| 6,398,398 B1 | 6/2002 | Moschkowitz | |
| 6,402,511 B1 | 6/2002 | Calderwood | |
| 6,417,917 B1 | 7/2002 | Jung et al. | |
| 6,419,483 B1 | 7/2002 | Adam | 433/29 |
| 6,439,888 B1 | 8/2002 | Boutoussov et al. | |
| 6,465,961 B1 | 10/2002 | Cao | |
| 6,468,077 B1 | 10/2002 | Melikechi et al. | |
| 6,478,447 B2 | 11/2002 | Yen | |
| 6,482,004 B1 | 11/2002 | Senn et al. | |
| 6,485,301 B1 | 11/2002 | Gemunder et al. | |
| 6,511,317 B2 | 1/2003 | Melikechi et al. | |
| 6,511,321 B1 | 1/2003 | Trushkowsky et al. | |
| 6,514,075 B1 | 2/2003 | Jacob | |
| 6,522,086 B2 | 2/2003 | Gemunder et al. | 315/291 |
| 6,611,110 B1 | 8/2003 | Fregoso | 315/224 |
| 6,635,363 B1 | 10/2003 | Duclos et al. | 428/690 |
| 6,666,875 B1 | 12/2003 | Sakurai et al. | 606/169 |
| 6,692,251 B1 | 2/2004 | Logan et al. | |
| 6,692,252 B2 | 2/2004 | Scott | |
| 6,702,576 B2 | 3/2004 | Fischer et al. | 433/29 |
| 6,709,128 B2 | 3/2004 | Gordon et al. | |
| 6,719,558 B2 | 4/2004 | Cao | |
| 6,719,559 B2 | 4/2004 | Cao | |
| 6,755,647 B2 | 6/2004 | Melikechi et al. | 433/29 |
| 6,755,648 B2 | 6/2004 | Cao | |
| 6,783,362 B2 | 8/2004 | Cao | 433/29 |
| 6,890,175 B2 | 5/2005 | Fischer et al. | 433/29 |
| 6,940,659 B2 | 9/2005 | McLean et al. | 359/709 |
| 2001/0038992 A1 | 11/2001 | Otsuka | |
| 2001/0046652 A1 | 11/2001 | Ostler | 433/29 |
| 2001/0055451 A1 | 12/2001 | Kuhara et al. | |
| 2002/0073921 A1 | 6/2002 | Russell et al. | |
| 2002/0085372 A1 | 7/2002 | Lehrer | |
| 2002/0093833 A1 | 7/2002 | West | |
| 2002/0102513 A1 | 8/2002 | Plank | |
| 2002/0115037 A1 | 8/2002 | Cao | 433/29 |
| 2002/0133970 A1 | 9/2002 | Gordon et al. | |
| 2002/0147383 A1 | 10/2002 | Weber et al. | |
| 2002/0163317 A1 | 11/2002 | Cao | |
| 2002/0167283 A1 | 11/2002 | Cao | |
| 2002/0168306 A1 | 11/2002 | Cao | |
| 2002/0168604 A1 | 11/2002 | Cao | |
| 2002/0168605 A1 | 11/2002 | Cao | |
| 2002/0168606 A1 | 11/2002 | Cao | |
| 2002/0168607 A1 | 11/2002 | Cao | |
| 2002/0168608 A1 | 11/2002 | Cao | |

| | | |
|---|---|---|
| 2002/0172912 A1 | 11/2002 | Cao |
| 2002/0172913 A1 | 11/2002 | Cao |
| 2002/0172914 A1 | 11/2002 | Cao |
| 2002/0172915 A1 | 11/2002 | Cao |
| 2002/0172916 A1 | 11/2002 | Cao |
| 2002/0172917 A1 | 11/2002 | Cao ............................ 433/29 |
| 2002/0175352 A1 | 11/2002 | Cao |
| 2002/0175628 A1 | 11/2002 | Cao |
| 2002/0177095 A1 | 11/2002 | Cao |
| 2002/0177096 A1 | 11/2002 | Cao |
| 2002/0177099 A1 | 11/2002 | Cao |
| 2002/0180368 A1 | 12/2002 | Cao |
| 2002/0181947 A1 | 12/2002 | Cao |
| 2002/0182561 A1 | 12/2002 | Cao |
| 2002/0182562 A1 | 12/2002 | Cao ............................ 433/29 |
| 2002/0187454 A1 | 12/2002 | Melikechi et al. |
| 2002/0187455 A1 | 12/2002 | Melikechi et al. |
| 2002/0190659 A1 | 12/2002 | Cao |
| 2002/0190660 A1 | 12/2002 | Cao |
| 2002/0197582 A1 | 12/2002 | Cao ............................ 433/29 |
| 2003/0001507 A1 | 1/2003 | Cao |
| 2003/0036031 A1 | 2/2003 | Lieb ............................ 433/29 |
| 2003/0038291 A1 | 2/2003 | Cao |
| 2003/0039119 A1 | 2/2003 | Cao |
| 2003/0039120 A1 | 2/2003 | Cao |
| 2003/0039122 A1 | 2/2003 | Cao |
| 2003/0040200 A1 | 2/2003 | Cao |
| 2003/0081430 A1 | 5/2003 | Becker ....................... 362/573 |
| 2003/0113684 A1 | 6/2003 | Scott ............................ 433/29 |
| 2003/0133203 A1 | 7/2003 | McLean et al. |
| 2003/0133298 A1 | 7/2003 | Cao |
| 2003/0142413 A1 | 7/2003 | McLean et al. |
| 2003/0147254 A1 | 8/2003 | Yoneda et al. |
| 2003/0147258 A1 | 8/2003 | Fischer et al. |
| 2003/0148242 A1 | 8/2003 | Fischer ........................ 433/29 |
| 2003/0152885 A1 | 8/2003 | Dinh |
| 2003/0186195 A1 | 10/2003 | Comfort et al. |
| 2003/0215766 A1 | 11/2003 | Fischer et al. |
| 2003/0218880 A1 | 11/2003 | Brukilacchio |
| 2003/0219693 A1 | 11/2003 | Cao |
| 2003/0219694 A1 | 11/2003 | Bianchetti et al. |
| 2003/0235800 A1 | 12/2003 | Qadar |
| 2004/0033033 A1 | 2/2004 | Hoshino et al. |
| 2004/0076921 A1 | 4/2004 | Gofman et al. ................ 433/29 |
| 2004/0101802 A1 | 5/2004 | Scott ........................... 433/29 |
| 2004/0121280 A1 | 6/2004 | Fischer et al. ................ 433/29 |
| 2004/0152038 A1 | 8/2004 | Kumagai et al. ............. 433/29 |
| 2004/0201980 A1 | 10/2004 | Fischer et al. ................ 362/84 |
| 2004/0203312 A1 | 10/2004 | Bortscheller et al. ......... 445/24 |
| 2004/0214131 A1 | 10/2004 | Fischer et al. ................ 433/29 |
| 2005/0042570 A1 | 2/2005 | Fischer et al. ................ 433/29 |
| 2005/0136372 A1 | 6/2005 | Fischer et al. ................ 433/29 |

OTHER PUBLICATIONS

U.S. Appl. No. 11/184,433, filed Jul. 19, 2005, Robert R. Scott.
U.S. Appl. No. 11/200,988, filed Aug. 10, 2005, Robert R. Scott.
U.S. Appl. No. 11/294,159, filed Dec. 5, 2005, Robert R. Scott.
U.S. Appl. No. 60/304,324, filed Jul. 10, 2001, Densen Cao.
"LUXoMAX the Latest News fron Akeda Dental," Akeda Dental A/S, www.akeda.dk (Oct. 1, 2001).
"New Sandia UV LEDs emit short-wavelength, high power output," Sandia Laboratories, http://www.eurekalert.org/pub_releases2003-11/dnl-nsu111803.php (Nov. 18, 2003).

* cited by examiner

DENTAL CURING DEVICE HAVING A HEAT SINK FOR DISSIPATING HEAT

BACKGROUND OF THE INVENTION

1. The Field of the Invention

The present invention generally relates to the field of light curing devices incorporating light sources and, more particularly, to the field of heat sinks configured for dissipating heat generated by the light sources of the light curing devices.

2. The Relevant Technology

In the field of dentistry, dental cavities are often filled and/or sealed with photosensitive compounds that are cured when they are exposed to radiant energy, such as visible or ultraviolet light. These compounds, commonly referred to as light-curable compounds, are placed within dental cavity preparations or onto dental surfaces where they are subsequently irradiated by a light-curing dental device.

Many light-curing devices are configured with a fiber optic wand for directing light from a light source into a patient's mouth. The light source may comprise, for example, a lamp, a halogen bulb or a light-emitting diode (LED). One end of the fiber optic wand is placed close to the light source so that the light emitted from the light source will be directed into the fiber optic wand. One problem with fiber optic wands is that they are generally unable to capture all of the light that is generated by the light source, particularly light emitted by LEDs, which may be emitted at angles of up to about 120°. Another problem is that fiber optic wands, being essentially solid glass, are relatively heavy and bulky.

One method for overcoming the limitations of fiber optic wands and for generally improving the lightness and efficiency of the light-curing devices is to place the light source(s) of the light-curing device at the end of the light-curing device that is placed next to the composition being cured. Although this addressed problems associated with fiber optic wands, the proximity of the light source(s) to the patient's mouth creates its own problems. For example, heat generated by the light source(s) at the tip of the light-curing device can cause patient discomfort when the tip of the light-curing device happens to come in contact or immediate proximity to the sensitive mouth tissues of the patient. Accordingly, it is desirable to minimize the heat at the tip of the light-curing device.

One method for minimizing the heat at the tip of the light-curing device is to mount the light source(s) on a heat sink that can conduct heat away from the tip of the light-curing device. The ability of a heat sink to diffuse heat is generally controlled by the material properties and geometries of the heat sink. The arrangement and geometries of the mounting surfaces of the heat sink are also important factors to consider when determining how efficiently the heat sink will be able to diffuse heat.

Recently, light-curing devices have been developed that utilize multiple light sources. One such design incorporates a plurality of LEDs that are mounted on one or more heat sinks. Although a heat sink is incorporated within this design, the bulk of the heat sink mass is located in the vicinity of the LEDs near the patient's mouth. Among other things, the switches and circuitry within the curing light housing prevent extending the heat sink beyond a certain point in the curing light. Thus, a majority of heat is still generated and accumulated near the tip of the curing light that is inserted into the patient's mouth. It would therefore be an improvement in the art to provide improved heat sink configurations to more effectively dissipate heat away from the tip of a dental curing device.

BRIEF SUMMARY OF THE PREFERRED EMBODIMENTS

The present invention is directed to a dental curing light having a heat sink specifically configured for effectively dissipating heat generated by one or more LEDs away from the tip of the dental curing device.

According to one embodiment, the dental curing light comprises an elongate hollow wand housing having a proximal first end, a distal second end, at least one LED disposed at the distal second end of the wand housing, electronic circuitry disposed within the wand housing between the first and second ends, and a heat sink within the wand housing.

The heat sink of this embodiment includes a metallic portion adjacent the one or more LEDs and extending partially through the wand housing, and a thermally conductive polymer-based (e.g., epoxy) portion adjacent to the metallic portion. The thermally conductive polymer-based portion at least partially surrounds the electronic circuitry and extends through a portion of the wand housing that is gripped by the user when in use.

Forming the heat sink from a metallic portion and a polymer-based portion allows a larger heat sink than would otherwise be possible. The thermally conductive polymer-based portion of the heat sink can be adjacent to the electronic circuitry of the dental curing device without causing electrical conductivity problems (e.g., short circuiting of the circuitry) that a metallic heat sink would cause. Unlike metals, heat-conductive polymer can be injected into the wand cavity at a relatively cool temperature (e.g., room temperature) so as to encapsulate the circuitry without damaging it.

Because the heat sink can extend through substantially the entire length of the wand, it can efficiently draw heat away from the tip of the dental curing device down towards the portion of the wand gripped by the user. Dissipating the heat away from the tip provides a greater degree of comfort for the patient.

According to one embodiment, the metallic portion of the heat sink is separated from the wand housing by an air gap. The air gap provides insulation, resulting in less heat diffusing out of the housing wand of the dental curing device in the region around the tip of the curing device, resulting in a cooler tip and greater comfort for the patient. In addition, at least a portion of the heat-conductive polymer portion of the heat sink may directly contact the wand housing in order to selectively cause the wand housing to dissipate heat away from the patient's mouth and toward the part of the wand housing gripped by the dental practitioner. This, in turn, allows the dental practitioner's hand to further draw heat away from the patient's mouth during use.

The metallic portion of the heat sink may comprise one or more of aluminum, brass, copper, steel, silver or other thermally conductive metal, or a ceramic based on at least one metal oxide. The polymer-based heat sink portion may comprise one or more polymers (e.g., epoxy or silicone) that are sufficiently thermally conductive so as to further conduct heat away from the metallic heat sink portion. The polymer-based heat sink portion may be a solid, liquid, gel or other desired physical state.

In one embodiment, the polymer or resin is filled with a heat-conductive filler (e.g., carbon fibers, graphite particles, ceramics, and the like) in order to increase the thermal conductivity of the polymer-based heat sink portion. An example of a filled thermally conductive polymer is COOL POLYMER, which comprises a filled polyphenylene sulfide. Virtually any polymer can be made thermally conductive by filling it with a sufficient quantity of a thermally conductive filler.

In the case where the polymer-based heat sink portion is intended to make direct contact with the electronic circuitry of the curing device, the polymer-based heat sink portion will preferably not contain electrically conductive metals or other materials (at least on the vicinity of the circuitry) that would cause the polymer-based heat sink portion to short circuit the curing device.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

A detailed description of the curing device of the invention will now be provided with specific reference to figures illustrating preferred embodiments of the invention. It will be appreciated that like structures will be provided with like reference designations.

In general, the dental curing light comprises an elongate hollow wand housing having a proximal first end, a distal second end, at least one light source disposed at the distal second end of the wand housing, electronic circuitry disposed within the wand housing between the first and second ends, and a heat sink disposal within the wand housing.

The heat sink comprises a metallic heat sink portion adjacent the LED that extends partially through the wand housing, and a thermally conductive polymer-based heat sink portion adjacent to the metallic heat sink portion adjacent to, or that at least partially surrounds, the electronic circuitry. The polymer-based heat sink portion extends through the portion of the wand housing that is gripped by the user.

The term "light source" includes any light source known in the art suitable for use with dental curing lights, examples of which include incandescent lamps, halogen bulbs, light-emitting diodes (LEDs), and LED arrays. The term "LED light source" includes the electrical components of the LED as well as the integral lens or micro lens of the typical LED structure.

Figure 1:
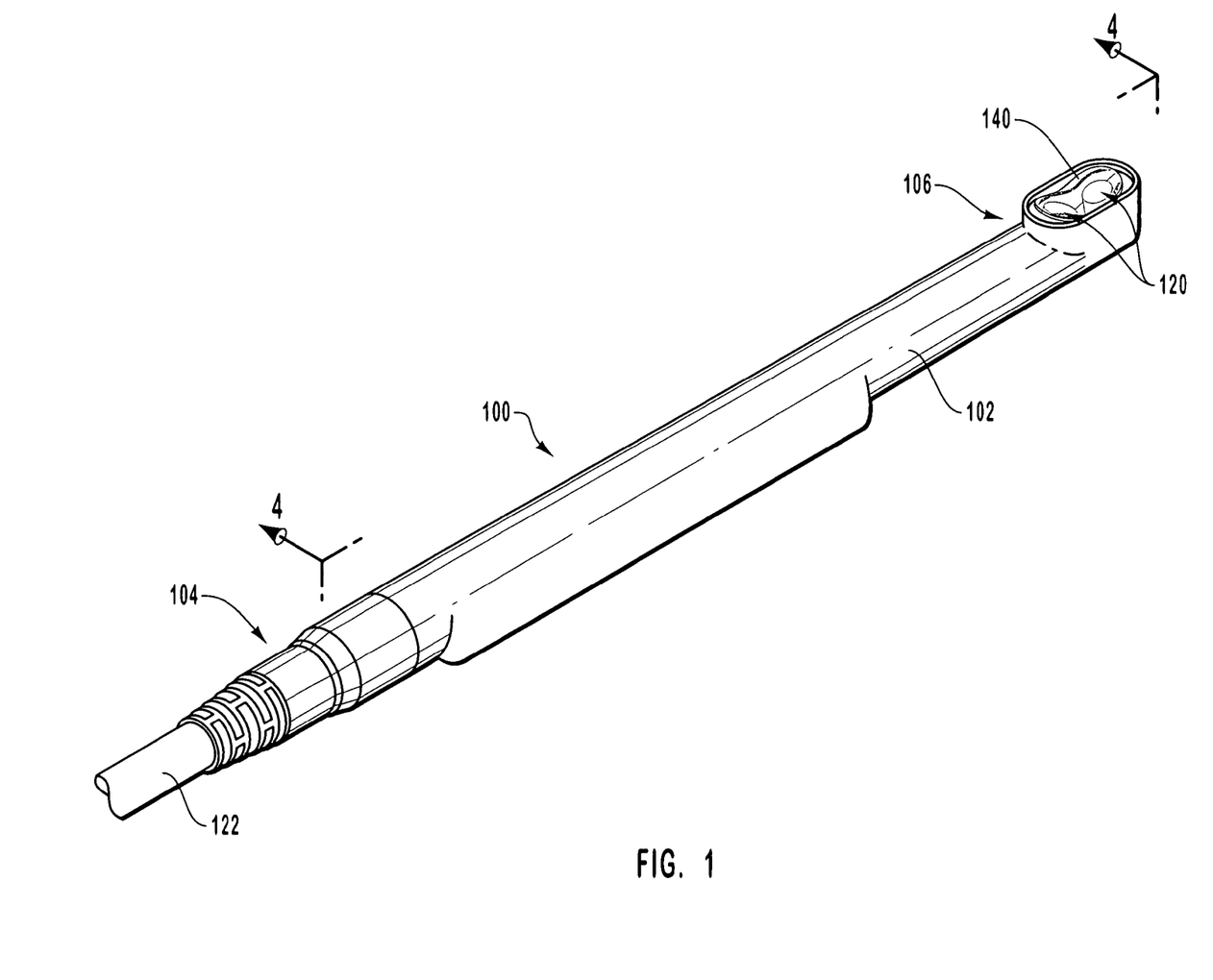
FIG. 1 is a bottom perspective view of a dental curing device according to the invention.

Reference is first made to FIG. 1, which is a bottom perspective view of one embodiment of a dental device 100. As shown, the dental device 100 includes an elongate housing 102 that extends between a proximal first end 104 and a distal second end 106. Although the housing 102 is shown to be sleek and slender, it will be appreciated that the housing 102 of the dental device 100 may comprise any desired shape and size.

A light source 120 disposed at the distal end 106 of the dental device 100 is configured to emit light suitable for curing light-curable compounds, such as, for example, during dental restoration procedures. The light source 120, as shown, includes two LEDs. Although only two LEDs are shown, it will be appreciated that the light source 120 may also include more or less than two LEDs or other light sources. The light source 120 may also include an LED array, a plurality of LED arrays, and any combination of LEDs and LED arrays. The device 100 may also include a lens 140 sized and configured so as to cover the light source 120 at the distal end 106 of the body 102 and to focus light emitted by the light source 120.

According to one embodiment of the invention, the light source 120 and the distal end 106 of the elongate housing 102 are sized and configured so as to be easily inserted into the mouth of a patient, thereby enabling light generated by the light source 120 to be directly emitted into the patient's mouth without first passing through an elongated light guide (e.g., a fiber optic wand), as required by many conventional light curing devices.

According to one embodiment, the light source 120 is powered by a remote electrical power supply (not shown), which may include, but is not limited to, the power outlet of a wall receptacle, a battery, a generator, a transformer or any other source capable of supplying power to the dental device. A power cord 122 connected at the proximal end 104 of the dental device 100 operably connects the remote power supply with the dental device 100.

According to one alternative embodiment (not shown), the proximal end 104 of the dental device is not connected to a power cord 122, but rather the dental device 100 is equipped with an integral battery pack that is capable of powering the dental device 100 and energizing the light source. The battery pack is advantageously rechargeable (e.g., by direct electrical contact or by induction).

Figure 2:
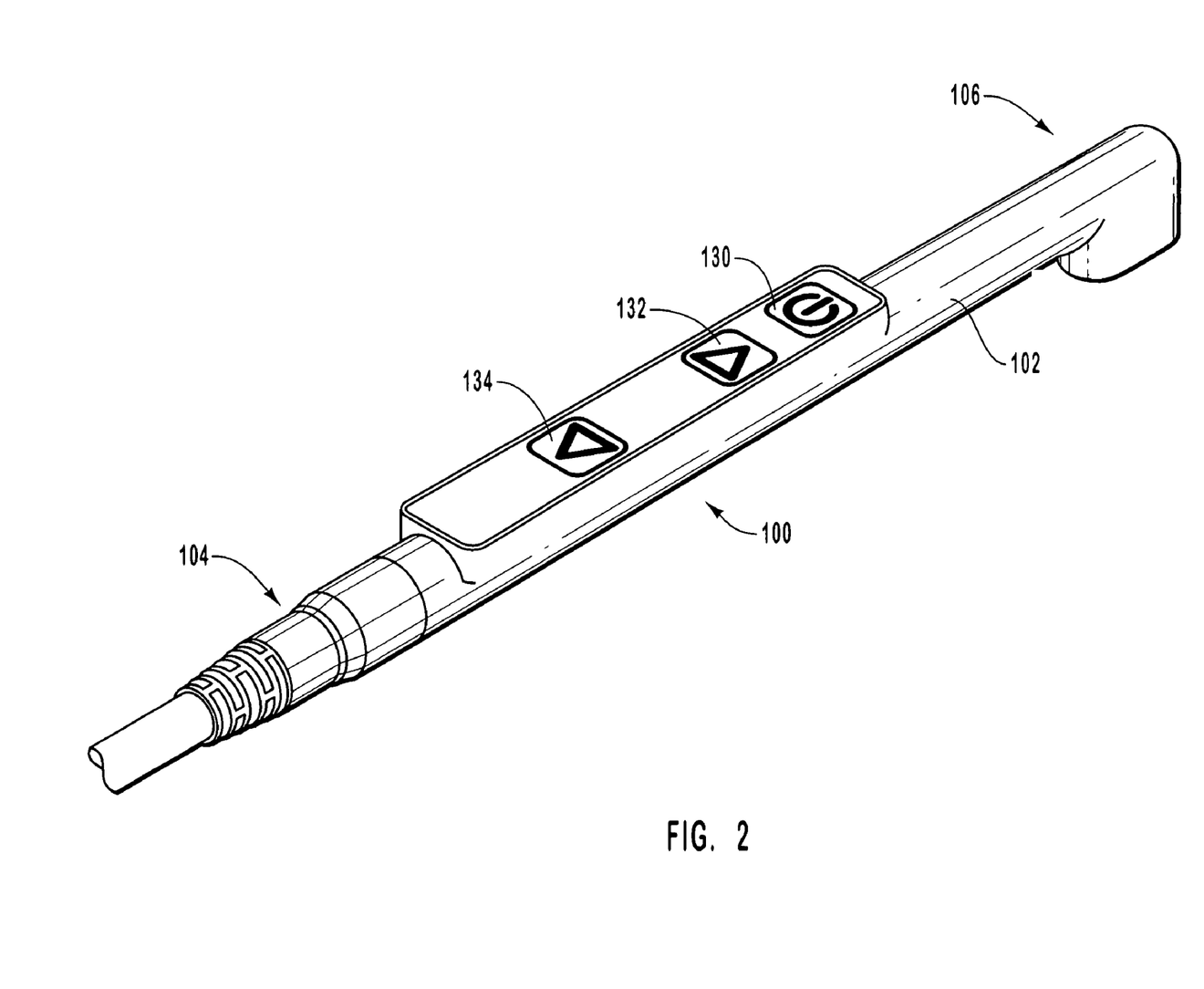
FIG. 2 is an top perspective view of the device of FIG. 1.

FIG. 2 is a top perspective view of the dental device 100 shown in FIG. 1 and further illustrates controls that are disposed on the elongate housing 102 of the dental device 100. According to this embodiment, the controls are configured to enable a dental practitioner to control the activation of the light source 120.

According to this embodiment, the controls preferably include three different buttons 130, 132, 134. The first button 130, when depressed, selectively activates and deactivates the light source 120. In one embodiment, first button 130, when depressed, may activate the light source for a predetermined duration of time, such as, for example, 15 seconds, thereby enabling the dental practitioner to use the dental device 100 without having to continuously depress button 130 during use. The second and third buttons 132, 134 can be designed to increase or decrease the predetermined duration of time light is emitted by a desired increment of time, such as, for example, by 5 second increments. Alternatively, second and third buttons 132, 134 can be designed to selectively increase or decrease the intensity of light that is emitted. The buttons could alternatively be designed to switch between ramped, pulsed or continuous light output.

The curing light 100 may, of course, include any desired number and functionality of buttons or controls.

The controls are advantageously ergonomically mounted on the elongate housing 102 of the dental device 100 for ease of use. In particular, the controls are advantageously disposed on the body 102 in a manner which enables them to be manipulated by the thumb or finger of the dental practitioner. It will be appreciated, however, that the dental device 100 of the invention is not limited to any particular configuration or type of controls. Rather, the dental devices of the invention may be configured with any type of controls that are attached to the body of the dental device or that are remotely located away from the device, as desired.

Figure 3:
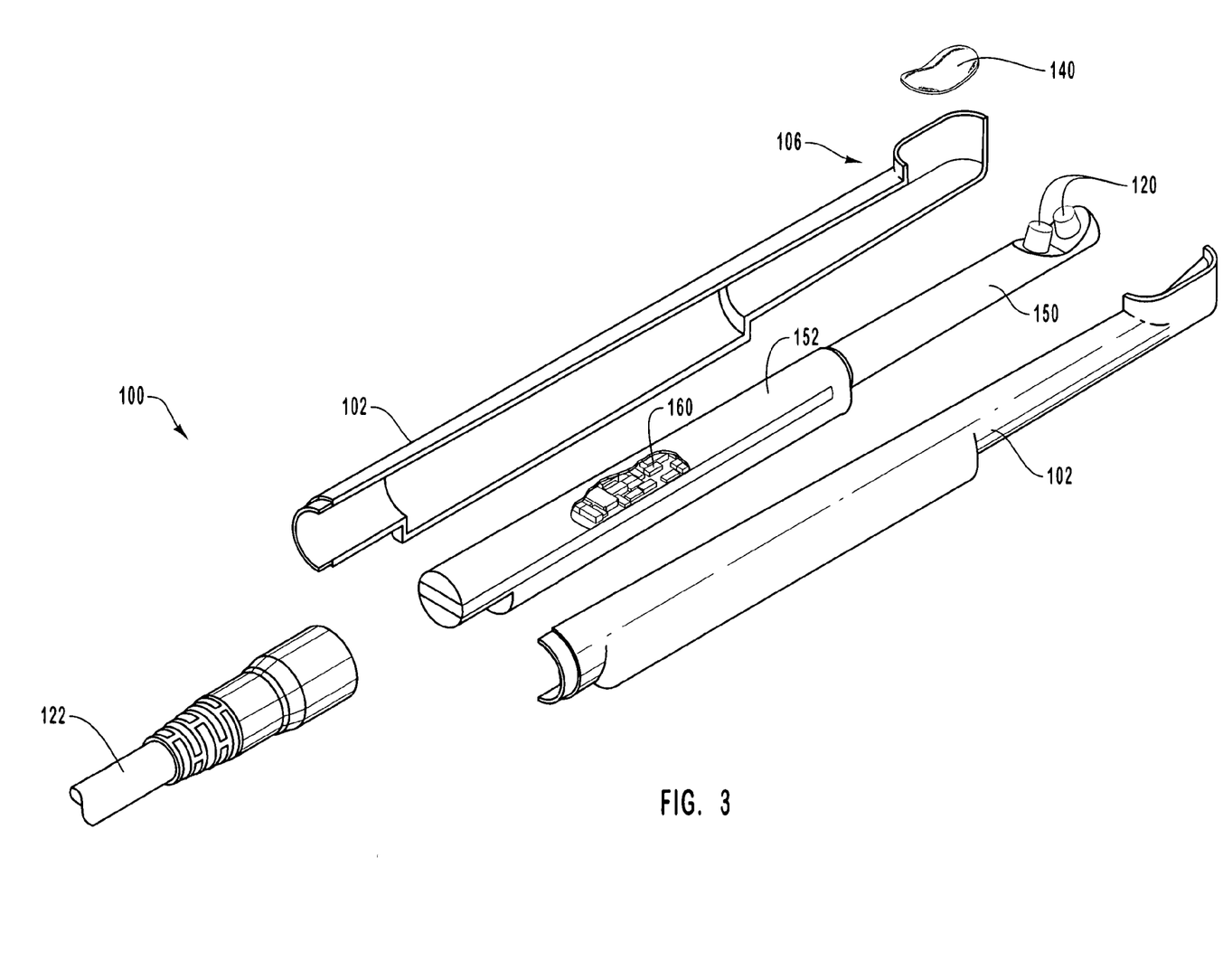
FIG. 3 is a partial exploded view of the dental curing device of FIGS. 1 and 2.

FIG. 3 is a partial exploded view of the dental curing device 100. As can be seen in this exploded view, the elongate housing 102 is hollow so as to allow room for the internal components of the dental device 100. The light source (e.g., LEDs) 120 may be mounted to a metallic heat sink portion 150. In any case, the metallic heat sink portion 150 is configured so as to be adjacent to the light source 120 so as to draw away excess heat produced by the light source 120.

The metallic heat sink portion 150 may be formed of any suitable metal or thermally conductive metal-based ceramic (e.g., based on one or more metal oxide). Suitable metals include aluminum, brass, copper, steel, or silver. Metallic materials may be used alone or combined into various suitable alloys, as known in the art. Being metallic, the metallic heat sink portion 150 has a relatively high thermal conductivity, effectively drawing heat from the LEDs away from the distal end 106 of the device 100.

The device 100 also includes electronic circuitry 160 for controlling the operation of the device through buttons 130, 132, and 134 (or alternative controls) as illustrated and described in conjunction with FIG. 2. Power may be provided to the electronic circuitry 160 through an electrical connection (not shown) to power cord 122. Additional wiring (not shown) to provide power and control between the electronic circuitry 160 and the LEDs 120 may also be included, as desired.

In order to provide additional heat sink capacity beyond what is provided by the metallic heat sink portion 150, a thermally conductive polymer-based heat sink portion 152 is located adjacent to the metallic heat sink portion 150. The polymer-based heat sink portion 152 at least partially surrounds, or is adjacent to, the electronic circuitry 160. Because the polymer-based heat sink portion 152 is thermally conductive, but preferably not electrically conductive, at least that portion that comes into contact with the electronic circuitry 160, it can surround and even touch the electronic circuitry without short circuiting the circuitry 160.

The polymer-based heat sink portion 152 may comprise one or more polymers (e.g., epoxy or silicone) that are sufficiently thermally conductive so as to further conduct heat away from the metallic heat sink portion 150. In one embodiment, the polymer or resin is filled with a heat-conductive filler (e.g., carbon fibers, graphite particles, ceramics, and the like) in order to increase the thermal conductivity of the polymer-based heat sink portion 152. The polymer-based heat sink portion may be a solid, liquid, gel or other desired physical state.

In the case where the polymer-based heat sink portion 152 is intended to make direct contact with the electronic circuitry of the curing device, the polymer-based heat sink portion 152 will preferably not contain electrically conductive metals or other materials (at least on the vicinity of the circuitry) that would cause the polymer-based heat sink portion 152 to short circuit the curing device. The polymer-based heat sink portion 152 may include electrically conductive metals or ceramics so long as it does not directly contact exposed electronic circuitry 160 (i.e., there is any insulating material or gap between the polymer-based heat sink portion 152 and the electronic circuitry 160).

Because of the relatively large surface area of the two heat sink portions 150 and 152, the metallic heat sink portion 150 and polymer-based heat sink portion 152 together draw heat away from the distal end of the device 100 more effectively than a metallic heat sink of smaller size by itself.

Figure 4:
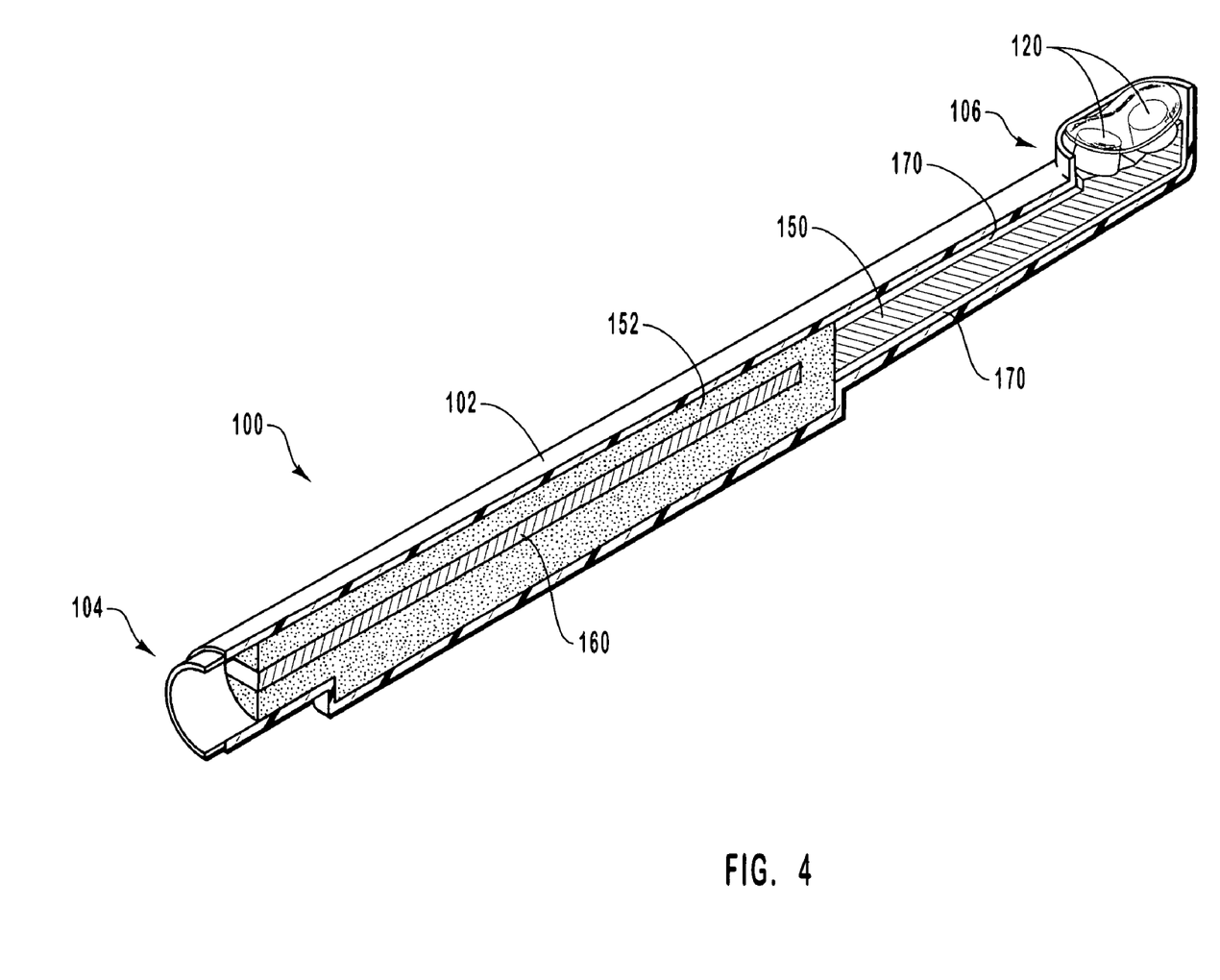
FIG. 4 is a cross sectional view of the dental curing device of FIGS. 1 and 2 taken along cutting line 4—4.

As illustrated in the cross sectional view of FIG. 4, there may be a heat-insulating layer 170 between the metallic heat sink portion 150 and the elongate housing 102. According to one embodiment, the heat-insulating layer 170 may be an air gap, although it could alternatively be filled with any known heat-insulating material (e.g., insulating ceramics or polymers). Providing a heat-insulating layer 170 surrounding the metallic heat sink portion 152 reduces the amount of heat that would otherwise be dissipated out of the distal end of the device 100. Reducing dissipation of heat at the distal end 106 of the curing light 100, which is nearest the patient's teeth, mouth, and other sensitive tissue, results in a more comfortable operation.

In one embodiment, there is no thermally insulating layer between the polymer-based heat sink portion 152 and the housing 102. This increases the amount of heat dissipation that is in the region of the housing 102 that is away from the patient's mouth. Channeling the heat so that it is dissipated away from the patient's mouth results in a more comfortable operation for the patient, as described above. Moreover, more efficiently dissipating heat when the housing 102 is gripped by the dental practitioner can act to further withdraw heat away from the patient's mouth by instead directing it toward the user's hand.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A dental curing light, comprising:
an elongated hollow housing having a proximal end and a distal end, with a handle portion disposed between the proximal and distal ends;
a light source disposed at the distal end of the housing;
electronic circuitry disposed within the handle portion of the housing for controlling the light source; and
a heat sink disposed within the elongated hollow housing for transferring heat generated by the light source away from the distal end and for dissipating the heat that is transferred away from the light source, said heat sink comprising first and second portions which are juxtaposed end-to-end and which together essentially fill the elongated hollow housing,
the first portion of the heat sink comprising a first elongated solid metallic portion having proximal and distal ends, said distal end in thermal contact with the light source and extending from the light source and essentially filling the hollow elongated housing from the distal end to the handle portion of the elongated housing;
the second portion of the heat sink comprising a second elongated portion comprised of a polymer-based material that is not electrically conductive, said second portion being juxtaposed and in thermal contact with the first elongated solid metallic portion at its proximal end, said second elongated portion extending through and essentially filling said handle portion of the hollow housing and surrounding at least a portion of the electronic circuitry contained therein.

2. A dental curing light, comprising:

an elongated hollow housing having a proximal end and a distal end, with a handle portion disposed between the proximal and distal ends;

a light source disposed at the distal end of the housing;

electronic circuitry disposed within the handle portion of the housing for controlling the light source; and a heat sink disposed within the elongated hollow housing for transferring heat generated by the light source away from the distal end and for dissipating the heat that is transferred away from the light source, said heat sink comprising first and second portions which are juxtaposed end-to-end and which together essentially fill the elongated hollow housing, the first portion of the heat sink comprising a first elongated solid metallic portion having proximal and distal ends, said distal end in thermal contact with the light source and extending from the light source and essentially filling the hollow elongated housing from the distal end to the handle portion of the elongated housing;

the second portion of the heat sink comprising a second elongated portion comprised of a polymer-based material that is not electrically conductive, said second portion being juxtaposed and in thermal contact with the first elongated solid metallic portion at its proximal end, said second elongated portion extending through and essentially filling said handle portion of the hollow housing and surrounding at least a portion of the electronic circuitry contained therein; and an insulating layer surrounding the first elongated solid metallic portion so as to insulate it from the housing.

3. A dental curing light as recited in claim 2, wherein said insulating layer comprises an air gap separating at least a portion of the first elongated solid metallic portion of the heat sink from the housing.

4. A dental curing light as recited in claims 1 or 2, the first elongated solid metallic portion of the heat sink comprising at least one of aluminum, brass, copper, steel, or silver.

5. A dental curing light as recited in claims 1 or 2, the first elongated solid metallic portion of the heat sink comprising a thermally-conductive ceramic comprising at least one metal oxide.

6. A dental curing light as recited in claims 1 or 2, the light source comprising at least one LED.

7. A dental curing light as recited in claims 1 or 2, further comprising a lens sized and configured so as to focus light emitted from the light source in a desired manner.

8. A dental curing light as recited in claims 1 or 2, the light source being powered by and external power source.

9. A dental curing light as recited in claims 1 or 2, further comprising an integral battery pack for powering the light source.

10. A dental curing light as recited in claims 1 or 2, wherein said housing comprises one or more controls for selectively activating the light source.

11. A dental curing light as recited in claims 1 or 2, wherein the second elongated polymer-based portion of the heat sink makes physical contact with the electronic circuitry.

12. A dental curing light as recited in claims 1 or 2, wherein the second elongated polymer-based portion of the heat sink comprises at least one of an epoxy-based or silicone-based resin.

13. A dental curing light as recited in claims 1 or 2, wherein the second elongated polymer-based portion of the heat sink comprises at least one polymer and at least one heat conductive filler.

14. A dental curing light as recited in claims 1 or 2, wherein the second elongated polymer-based portion of the heat sink comprises at least one of a solid, liquid or gel.

* * * * *